(12) United States Patent
Hintze

(10) Patent No.: US 6,307,079 B1
(45) Date of Patent: Oct. 23, 2001

(54) HYDROCARBON SOLUBLE, TIN FUNCTIONALIZED ALKALI METALS

(75) Inventor: Mark J. Hintze, Charlotte, NC (US)

(73) Assignee: Chemetall Foote Corporation, Kings Mountain, NC (US)

( * ) Notice: Subject to any disclaimer, the term of this patent is extended or adjusted under 35 U.S.C. 154(b) by 0 days.

(21) Appl. No.: 09/398,599

(22) Filed: Sep. 17, 1999

Related U.S. Application Data

(60) Provisional application No. 60/101,095, filed on Sep. 18, 1998.

(51) Int. Cl.$^7$ ............................................ C07F 7/22
(52) U.S. Cl. .............................. 556/87; 556/81; 556/95
(58) Field of Search .................... 556/81, 87, 95

(56) References Cited

U.S. PATENT DOCUMENTS 5,420,219 * 5/1995 Lawson et al. ....................... 526/340

OTHER PUBLICATIONS

J Oranometallic Chemistry by Kohler 334 pp 359–367, 1987.*
CA:106:155910 abs of Recl Trav Chim Pays–Bas by Kirms et al 105(10) pp 462–4, 1986.*
CA:97:92446 abs of Chem Ber by Kauffmann et al115(5) pp 1810–1817, 1982.*
CA:118:124684 abs of Synlett 11 pp 891–2 by Sato, 1992.*
Chemistry Letters pp 1897–1900 by Murayama, 1984.*
CA:88:191008 abs of J Organometal Chem 148(3) pp 257–66 by Jutzi, 1978.*
CA:123:256313 abs of J Am Chem Soc 1995 117 (12) pp 3389–404 By Koo, 1995.*
Bulletin Chem Soc Japan by Sato 66 pp 3825–3827, 1993.*

* cited by examiner

Primary Examiner—Jean F. Vollano
(74) Attorney, Agent, or Firm—Fulbright & Jaworski, LLP

(57) ABSTRACT

Tin lithium compounds of the formula RR'R"SnGM', wherein R, R' and R" may be the same or different and each comprises an alkyl, aryl, aralkyl or alkylaryl having from 1 to 15 carbon atoms and wherein each carbon atom may be unsubstituted or substituted, G is a substituted or unsubstituted branched, cyclic or straight chain hydrocarbon having from 1 to 20 carbon atoms, the substitutions comprising one or more aryl groups, and M' is an alkali metal comprising Li, Na or K, are prepared. These compounds are useful as initiators in anionic polymerization reactions.

5 Claims, No Drawings

HYDROCARBON SOLUBLE, TIN FUNCTIONALIZED ALKALI METALS

This application claims priority to provisional application 60/101,095, filed Sep. 18, 1998.

BACKGROUND AND SUMMARY OF THE INVENTION

Tin lithium compounds of the general formula

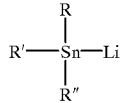

are known, wherein R, R' and R" are selected from alkyl, branched alkyl or phenyl. These are used as initiators in anionic polymerization reactions.

The tin functionality has been demonstrated to reduce hysteresis in elastomers and consequently give a tire with reduced rolling resistance such as described in EP 682 035 A2.

Presently, the most cost-effective method for making a tin lithium initiator is to react a triorganotin chloride with lithium metal. Unlike alkyllithiums, however, the formation of the tin lithium species requires the reaction to occur in a polar, aprotic solvent like tetrahydrofuran (THF).

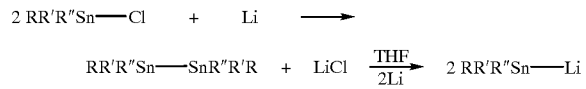

It has been found that a minimum mole ratio of 3:1 THF to tin is required in the synthesis. If the ratio is less than 3:1, some fraction of the reaction (proportional to the deficiency of THF) stops at the ditin stage. NMR analysis discloses that the tributyltin lithium is both monomeric and trisolvated in THF. (See Reich, H. J.; Borst, J. P.; Dykstra, R. R. Organometallics 1994, 13, 1–3). Attempts to remove the THF after the initiator has been synthesized leads to decomposition of the tin lithium back to the ditin compound. Based on the foregoing, THF or a similar Lewis base is required to produce this class of tin lithium initiators using the methods presently known in the art.

THF, as well as other solvents, present several problems. For example, Huang et al have shown that THF leads to increased vinyl content in polymers. Huang, Der-Chi; Tsiang, Raymond Chien-Chao J. Appl. Polym. Sci. 1996, 61(2), 333–342; see also Buzdugan, Emil; Ghioca, Paml Mater. Plast. 1995, 32(2), 127–32. Also, since polymerization reactions are typically carried out in hydrocarbon solvents, THF from the initiator contaminates the hydrocarbon recycle stream in polymer production plants. Therefore, hydrocarbon soluble, tin functionalized anionic initiators free of any Lewis base are desirable.

The present invention relates to a a new class of tin lithium compounds of Formula I

wherein R, R' and R" may be the same or different and each is independently selected from alkyl, aryl, aralkyl and alkylaryl having from 1 to 15 carbon atoms and wherein each carbon atom may be unsubstituted or substituted, G is a substituted or unsubstituted branched, cyclic or straight chain hydrocarbon having from 1 to 20 carbon atoms, the substitutions comprising one or more aryl groups, and M' is an alkali metal comprising Li, Na or K.

The present invention is also directed to a method for synthesizing tin functionalized alkali metal by reacting an organometallic composition of Formula (I)

with a compound having the formula (III)

XGX'            (III)

In Formula (I), R, R' and R" may be the same or different and are an alkyl, aryl, aralkyl, or alkylaryl having from 1 to 15 carbon atoms. Each carbon atom may be unsubstituted or substituted. M is an alkali metal selected from Li, Na and K.

In Formula (II), X and X' may be the same or different and each is a halogen. G is a substituted or unsubstituted branched, cyclic or straight chain hydrocarbon having from 1 to 20 carbon atoms, the substitutions comprising one or more aryl groups. The reaction of (I) and (II) forms compound of the Formula IV

wherein R, R', R", G and X' are as defined above, which is reacted with an alkali metal selected from Li, Na or K to form a compound (IV),

wherein and R, R', R", G and M' are described above. Formula (I) is a tin functionalized alkali metal useful as initiators in anionic polymerization reactions.

The present invention is also directed to a method for initiating an anionic polymerization reaction by conducting an anionic polymerization reaction in the presence of an initiator having the formula (I):

wherein R, R' and R" may be the same or different and each are independently selected from alkyl, aryl, aralkyl, and alkylaryl having from 1 to 15 carbon atoms and wherein each carbon atom may be unsubstituted or substituted, G is a substituted or unsubstituted branched, cyclic or straight chain hydrocarbon having from 1 to 20 carbon atoms, the substitutions comprising one or more aryl groups, and M' is an alkali metal comprising Li, Na or K.

The present invention also provides a method for reducing hysteresis in an elastomer by forming an elastomer by anionic polymerization of at least one monomer with an initiator of the formula (I).

wherein R, R' and R" may be the same or different and each is selected from an alkyl, aryl, aralkyl and alkylaryl having from 1 to 15 carbon atoms and wherein each carbon atom may be substituted or unsubstituted, G is a substituted or unsubstituted branched, cyclic or straight chain hydrocarbon having from 1 to 20 carbon atoms, wherein the substitutions may be one or more aryl groups, and M' is an alkali metal comprising Li, Na or K.

The present invention will now be described in more detail below.

DETAILED DESCRIPTION

The present invention relates to a new class of tin lithium compounds of Formula I RR'R"SnGM'    (I)

wherein R, R' and R" may be the same or different and each is independently selected from alkyl, aryl, aralkyl, alkylaryl, or heteroaryl having from 1 to 15 carbon atoms which may be substituted or unsubstituted. These R groups may be ethers or ketones as well, provided they do not interfere with use of the tin lithium compound in a polymerization reaction. G is a substituted or unsubstituted branched, cyclic or straight chain hydrocarbon having from 1 to 20 carbon atoms, the substitutions comprising one or more aryl groups, and M' is an alkali metal, preferably Li, Na or K. These compounds are substantially free from THF or other solvents that may interfere with their use in polymerization reactions, a common problem found in presently available initiators.

Preferably, R, R' and R" are $C_1$–$C_6$ alkyl, aryl, aralkyl or alkylaryl, and more preferably are $C_1$–$C_4$ alkyl, aryl, aralkyl or alkylaryl. Methyl, ethyl, propyl, isopropyl, n-butyl, i-butyl, and t-butyl are preferred groups, with methyl, ethyl, n-propyl and n-butyl being most preferred.

G is preferably a $C_1$–$C_6$ substituted or unsubstituted branched, cyclic or straight chain hydrocarbon, most preferably $C_1$–$C_3$. As with R, R' and R", methyl, ethyl, propyl, isopropyl, n-butyl, i-butyl, and t-butyl are preferred groups, with methyl, ethyl, n-propyl and n-butyl being most preferred.

M' is most preferably lithium.

The present invention is also directed to a method for synthesizing the tin functionalized alkali metal of formula I by reacting an organometallic composition of Formula (II)

RR'R"Sn—M    (II)

with a compound having the formula (III)

XGX'    (III)

wherein R, R' and R" are defined as above, i.e. they may be the same or different and are selected from alkyl, aryl, aralkyl, or alkylaryl having from 1 to 15 carbon atoms. Each carbon atom may be unsubstituted or substituted as defined above. M is an alkali metal selected from Li, Na and K.

In Formula (III), X and X' are halogen, and may be the same or different. Preferably X and X' are independently chlorine or bromine.

G is the same as defined above, and may be, for example, a substituted or unsubstituted branched, cyclic or straight chain hydrocarbon having from 1 to 20 carbon atoms, preferably the substitutions comprising one or more aryl groups. The reaction of (II) and (III) forms compound of the Formula IV RR'R"SnGX'    (IV)

wherein R, R', R", G and X' are as defined above, which is reacted with an alkali metal selected from Li, Na or K to form a the tin functionalized alkali metal of formula (I), RR'R"SnGM'    (I)

wherein and R, R', R", G and M' are as defined above.

The present invention is also directed to a method for initiating an anionic polymerization reaction with the compounds of Formula I by conducting an anionic polymerization reaction in the presence of an initiator of Formula (I):

RR'R"SnGM'    (I)

wherein R, R', R", G and M' are as defined above.

The present invention also provides a method for reducing hysteresis in an elastomer by forming an elastomer by anionic polymerization of at least one monomer with an initiator of the formula (I):

RR'R"SnGM'    (I)

wherein R, R', R", G and M' are as defined above.

The initiators of the present invention may be used in the synthesis of natural or synthetic rubbers, e.g. styrene butadiene rubber.

The compounds of the present invention, due to their preparation, do not contain THF or other solvents that interfere with their subsequent use in polymerization reactions, a decided advantage over the initiators presently available.

The following examples illustrate preferred embodiments of the invention.

DETAILED DESCRIPTION OF PREFERRED EMBODIMENTS

EXAMPLE 1

308.8 g (0333 mol) of a 32.04% solution of tributyl tin lithiumBu3SnLi in THF was transferred to a pressure equalized additional funnel that had been oven dried and purged with argon while cooling to room temperature. In an oven dried, argon purged one liter flask containing a stir bar was weighed 52.4 g of 3-bromo-1-chloropropane. The addition funnel was fitted to the flask and the flask and its contents placed in an ice/methanol bath. The entire apparatus was kept under positive argon pressure via a bubbler. The Bu3SnLi was added dropwise with stirring over a two-hour period. The solution was stirred overnight, washed with 200 ml of saturated $NaHCO_3$, extracted with methylene chloride and dried over $MgSO_4$. The solvent was evaporated giving a viscous, clear liquid.

NMR showed the expected triplet between 3 and 4 ppm from the two protons adjacent to the C 1 (FIG. 1). XRF demonstrated that the tin substituted alkyl chloride was the major product rather than the corresponding bromide (FIGS. 2 and 3). A single reference was found in the literature for the preparation of tributyltin substituted chloropropane. Suggs, J. William; Lee, Ken S. J. Organomet. Chem. 1986, 288, 297–309. The synthesis called for using HMPA in addition to THF. However, HMPA proved to be unnecessary since the yield was 92%. The same reaction was successfully performed using 3-bromo-1 -chloro-2-methylpropane as well as 1,3-dichloropropane.

Metallation Reaction

The tin substituted chloropropane was then lithiated in hexane as follows:

Into a three neck, 50 ml, oven dried round bottom flask, containing a stir bar and purged with argon was weighted 0.37 g of Li and 20 ml of hexane. While under positive argon pressure, the flask was fitted with a condenser and a thermometer. The flask and its contents were heated until the hexane was refluxing. In a vial was placed 9.7 g of the 3-tributyltin-1-chloropropane and 6 ml of hexane. This was mixed and placed in a syringe and then added dropwise to the reflexing hexane/Li. Once the addition was complete, the mixture was allowed to stir and was refluxed for an additional ten minutes. The heat was removed and the flask allowed cooling and stirring for ten minutes before sampling. The NMR showed the starting material and had been consumed.

The reaction is shown below:

Bu₃SnC₃H₆Cl+2Li hexane→Bu₃SnC₃H₆Li +LiCl

The filtered product titrated as 18% by weight. To see if a higher concentration could be achieved the reaction was run again so as to nearly double the concentration. The second run titrated at 31.04% by weight. In both experiments, the triplet at 3.3 ppm from the two protons adjacent to the chloride group moved upfield to −0.7 ppm (FIG. 4). Both the shift and positions of the protons in the starting material and lithiated product are analogous to what occurs when n-butylchloride is converted to n-butyllithium. So the reactions were easy to monitor and judge complete. Presence of tin in the lithiated initiator was confirmed by 119Sn NMR.

All data confirms the synthesis of a tin functionalized propyllithium, a new class of anionic initiators capable of introducing tin at one terminus of a polymer chain.

EXAMPLE 2

Tin functionalized polybutadiene was prepared by reacting 1 mole of butadiene in 300 mls cyclohexane and heating to 50° C. 0.083 moles of the initiator produced in Example 1, i.e. Bu₃SnC₃H₆Li is injected while stirring vigorously. Heating and stirring is continued for 2 hours. After 2 hours the reaction is quenched with methanol and the tin functionalized polybutadiene was recovered. The reaction is described below:

Tin functionalized polybutadiene

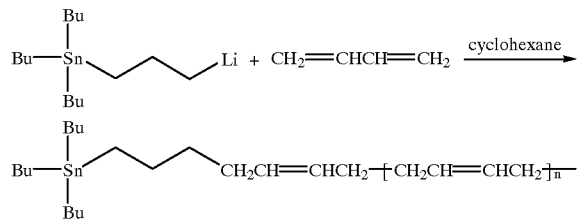

EXAMPLE 3

Tin functionalized polyisoprene was prepared according to the process of Example 2, except that isoprene was used as the starting monomer and the solvent was hexane. The reaction is described below:

Tin functionalized polyisoprene

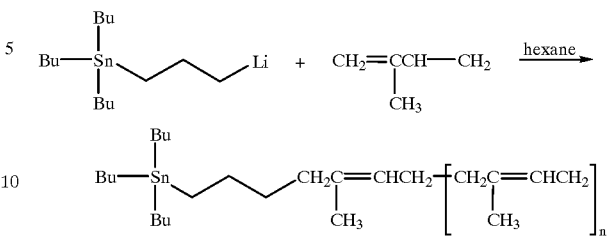

Other facets of the invention will be clear to the skilled artisan, and need not be set out here. The terms and expression which have been employed are used as terms of description and not of limitation, and there is no intention in the use of such terms and expression of excluding any equivalents of the features shown and described or portions thereof, it being recognized that various modifications are possible within the scope of the invention.

I claim:

1. A method for synthesizing a tin finctionalized alkali metal, comprising the steps of
   a. reacting an organometallic compound having the formula

RR'R"Sn–M          (I)

wherein R, R' and R" may be the same or different and each is a member independently selected from the group consisting of alkyl, aryl, aralkyl, and alkylaryl having from 1 to 15 carbon atoms and wherein each carbon atom may be unsubstituted or substituted, and M is an alkali metal selected form the group consisting of Li, Na or K, with a compound having the formula

XGX'          (II)

wherein X and X' may be the same or different and each comprises a halogen, and G is a substituted or unsubstituted branched, cyclic or straight chain hydrocarbon having from 1 to 20 carbon atoms, wherein the substitution is at least one aryl group, forming thereby a compound (Ill)

RR'R"SnGX'          (III)

and
   b. reacting compound (III) with an alkali metal comprising Li, Na or K to form the tin functionalized alkali metal of formula (IV)

RR'R"SnGM'          (IV)

wherein M' is Li, Na or K.

2. A method as claimed in claim 1, wherein R, R' and R" are each butyl.
3. A method as claimed in claim 2 wherein M and M' are each lithium.
4. A method as claimed in claim 3 wherein G is alkyl having 3 to 6 carbon atoms.
5. A method as claimed in claim 4 wherein G is propyl.

* * * * *